(12) United States Patent
Banholzer et al.

(10) Patent No.: US 6,891,042 B2
(45) Date of Patent: *May 10, 2005

(54) INDUSTRIAL PROCESS FOR PREPARING TROPENOL

(75) Inventors: Rolf Banholzer, Stuttgart (DE); Gisela Bodenbach, Ummendorf (DE); Andreas Mathes, Ockenheim (DE); Helmut Meissner, Ingelheim (DE); Peter Specht, Ober-Hilbersheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/764,922

(22) Filed: Jan. 26, 2004

(65) Prior Publication Data

US 2004/0158069 A1 Aug. 12, 2004

Related U.S. Application Data

(63) Continuation of application No. 10/448,493, filed on May 29, 2003, now Pat. No. 6,747,153.
(60) Provisional application No. 60/407,121, filed on Aug. 30, 2002.

(30) Foreign Application Priority Data

May 31, 2002 (DE) .......... 102 24 091

(51) Int. Cl.$^7$ .......... C07D 451/02; C07D 451/06; C07D 451/10
(52) U.S. Cl. .......... 546/90; 546/91; 546/127; 546/131
(58) Field of Search .......... 546/90, 131, 127, 546/91

(56) References Cited

U.S. PATENT DOCUMENTS 6,610,849 B2   8/2003   Sobotta et al.

OTHER PUBLICATIONS

Sheehan et al. J. Org. Chem. 1954, 19:270–6.*
Achari et al. Planta Medica. 1972, 22(1):38–41.*
Al–Said et al. Pytochemistry. 1989, 28(2):671–3.*
Buchi et al. J. Org. Chem. 1977, 42(12):2193–2194.*
Chu, G. et al; "Synthesis of 6,7–dehydrotorpiine"; Database Access No. 125:248172; XP002250968.
Sobotta, R. et al; "Process for the Manufacture of Tropenol"; U.S. Appl. No. 10/160,702; filed Jun. 3, 2002.
Bremner, J. B.; "Alkaioids As Starting Materials For Synthesis: The Use Of Scopolamine And Castanospermine"; ACGC Chem. Res. Comm.; vol. 11, 2000, pp. 20–28.
Bremner, J. B. et al; "A Meisenheimer Rearrangement Approach To Bridgehead Hydroxylated Tropane Alkaloid Derivatives"; Tetrahedron Letters, vol. 37, No. 1, 1996, pp. 97–100.
Aberle, N. S. et al; "Parallel modification of tropane alkaloids"; Tetrahedron Letters 42 (2001), pp. 1975–1977.

* cited by examiner

*Primary Examiner*—Evelyn Mei Huang
(74) *Attorney, Agent, or Firm*—Michael P. Morris; Mary-Ellen M. Devlin; Andrea D. Small

(57) ABSTRACT

The invention relates to a new industrially useable process for preparing tropenol, optionally in the form of the acid addition salts thereof.

4 Claims, No Drawings

INDUSTRIAL PROCESS FOR PREPARING TROPENOL

RELATED APPLICATIONS

This application is a continuation of U.S. patent application Ser. No. 10/448,493, filed May 29, 2003, now U.S. Pat. No. 6,747,153 which application claims benefit of U.S. Provisional Application Ser. No. 60/407,121, filed on Aug. 30, 2002, and said applications are herein incorporated by reference in their entirety.

FIELD OF THE INVENTION

The invention relates to a new industrially useable process for preparing tropenol, optionally in the form of the acid addition salts thereof.

BACKGROUND TO THE INVENTION

The compound tropenol is known from the prior art and has the following chemical structure:

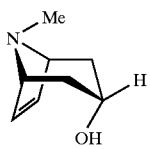

(I)

The compound may be used as a starting compound for preparing pharmacologically valuable compounds. For example, the compounds tiotropium bromide, ipratropium bromide or also BEA2108 may be mentioned in this context. These pharmacologically valuable substances are characterized by the following chemical structures:

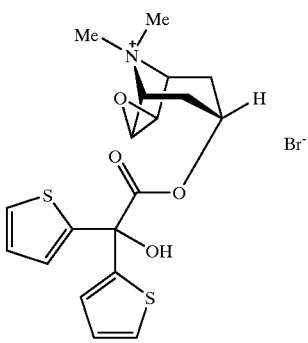

tiotropium bromide

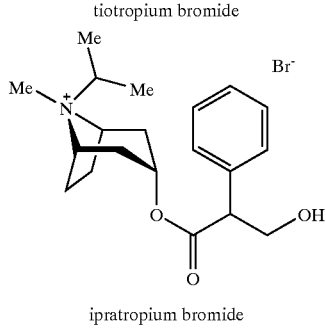

ipratropium bromide

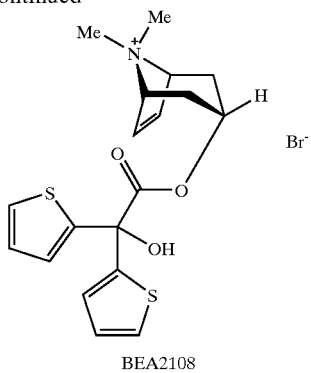

BEA2108

Because of the high degree of efficacy of the above compounds they have to be made available in as pure form as possible using efficient methods of synthesis. The stringent purity requirements, in particular, with which compounds intended for therapeutic use generally have to comply, demand the lowest possible levels of contaminant in the starting compounds. If materials which contain relatively high levels of impurities are used as starting compounds, purification of the end product is often difficult as any impurities introduced at the beginning often cannot easily be removed at later stages of synthesis or only at the expense of substantial losses of yield. This is particularly the case when the by-products or impurities present only differ slightly structurally from the main products in question.

Against this background the problem of the present invention is to provide a method of synthesis which allows industrial production of tropenol, preferably in the form of one of the acid addition salts thereof, in a good yield and particularly with a high degree of purity.

DETAILED DESCRIPTION OF THE INVENTION

The problem defined above is solved by the invention described hereinafter.

The present invention accordingly relates to an industrial process for preparing tropenol of formula (I)

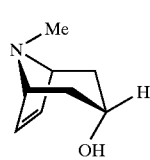

(I)

optionally in the form of the acid addition salts thereof, characterized in that a compound of formula (II)

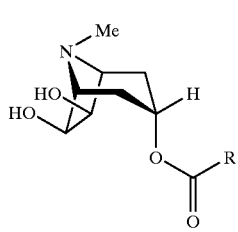

(II)

wherein

R denotes a group selected from $C_1$–$C_4$-alkyl, $C_2$–$C_6$-alkenyl and $C_1$–$C_4$-alkylene-phenyl, each of which may be substituted by hydroxy or $C_1$–$C_4$-alkoxy, optionally in the form of the acid addition salts thereof as well as optionally in the form of the hydrates thereof in a suitable solvent, is reacted with a formamide-acetal of formula (III)

wherein
R' denotes $C_1$–$C_4$-alkyl and R" denotes a group selected from $C_1$–$C_4$-alkyl and $C_1$–$C_4$-alkylene-phenyl, to obtain a compound of formula IV

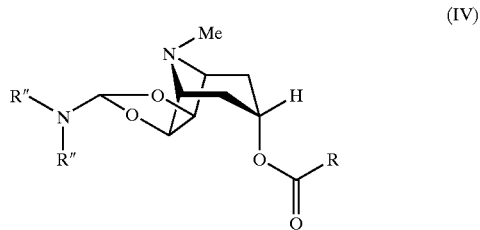

wherein the groups R, R' and R" may have the meanings given above, this is then converted by decarboxylation into an ester of formula (V)

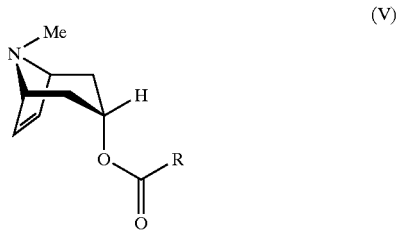

wherein R may have the meanings given above, and lastly this ester is saponified to obtain the compound of formula (I) which is optionally converted into an acid addition salt by reaction with a suitable acid.

Preferably, the present invention relates to an industrial process for preparing tropenol of formula (I), optionally in the form of the acid addition salts thereof, which is characterized in that a compound of formula (II) wherein R denotes $C_1$–$C_4$-alkyl or $C_2$–$C_4$-alkenyl is used as starting material, optionally in the form of the acid addition salts thereof and optionally in the form of the hydrates thereof, and wherein, in the formamideacetal of formula (III) used, the groups R' denote methyl or ethyl and the groups R" represent methyl, ethyl or propyl.

Most preferably, the present invention relates to an industrial process for preparing tropenol of formula (I), optionally in the form of the acid addition salts thereof, preferably in the form of its hydrochloride, which is characterized in that a compound of formula (II) wherein R denotes 1-propenyl, 2-propenyl, 1-buten-1-yl, 1-buten-2-yl, 1-buten-3-yl, 1-buten-4-yl, 2-buten-1-yl or 2-buten-2-yl is used as starting material, optionally in the form of the acid addition salts thereof as well as optionally in the form of the hydrates thereof and wherein in the formamide-acetal of formula (III) used the groups R' and R" represent methyl or ethyl, preferably methyl.

Most preferably, the compound of formula (II) used is the compound wherein R denotes 2-buten-2-yl. This compound is also known by the name meteloidin in the prior art.

The term $C_1$–$C_4$-alkyl within the scope of the present invention denotes branched or unbranched alkyl groups with up to 4 carbon atoms. Examples include methyl, ethyl, n-propyl, iso-propyl, n-butyl, sec-butyl, iso-butyl and tert-butyl. The term $C_1$–$C_4$-alkylene-phenyl within the scope of the present invention denotes phenyl which is linked via a branched or unbranched alkylene bridge having up to 4 carbon atoms. Examples include benzyl, phenyl-2-ethyl, phenyl-1-ethyl, phenyl-3-propyl, phenyl-2-propyl- etc. Both the $C_1$–$C_4$-alkyl groups and also the $C_1$–$C_4$-alkylene-phenyl groups may, unless otherwise specified, be substituted by one or more hydroxy and/or $C_1$–$C_4$-alkyloxy groups.

By $C_2$–$C_6$-alkenyl are meant within the scope of the present invention branched or unbranched alkenyl groups with 2 to 6 carbon atoms which have at least one double bond. Examples include vinyl, 1-propenyl, 2-propenyl, 1-buten-1-yl, 1-buten-2-yl, 1-buten-3-yl, 1-buten-4-yl, 2-buten-1-yl, 2-buten-2-yl, butadien-1-yl, butadien-2-yl etc.

Unless otherwise stated, within the scope of the present invention the term acid addition salts refers to the salts formed with the acids hydrochloric acid, hydrobromic acid, phosphoric acid, sulphuric acid, tetrafluoroboric acid or hexafluorophosphoric acid, preferably hydrochloric acid or hydrobromic acid.

According to the invention, the following procedure may be followed for performing the process for preparing tropenol according to the invention.

The compound of formula (III) is placed in a suitable reaction vessel. Usually at least 1 mol of the compound (III) is used per mol of the compound of formula (II) to be reacted. Preferably, between 1.01 and 5.0 mol, preferably between 1.1 and 4.0 mol, most preferably between 1.5 and 3.0 mol of the compound (III) are put in per mol of the compound (III) to be reacted. Then the compound of formula (II) is added batchwise with stirring. After the addition has ended the mixture obtained is heated preferably to a temperature of above 40° C., preferably more than 50° C., most preferably more than 60° C. In the course of the reaction the alcohol R'—OH is released. It is preferably removed from the reaction equilibrium by distillation. This distillation may optionally be carried out under reduced pressure. If the compound of formula (III) used is the compound wherein R' denotes methyl, the temperature is preferably adjusted to a range from about 55–90° C., more preferably from about 60–85° C. After the reaction has ended the compound of formula (III) which was optionally used in excess is removed by distillation under reduced pressure. To do this the mixture obtained is preferably heated to a temperature of above 40° C., preferably above 50° C., and a vacuum of 100 mbar or less, preferably 60 mbar or less, most preferably 40 mbar or less is applied.

The residue remaining (crude product of general formula (IV)) is then taken up with stirring in a suitable solvent, preferably in a polar organic solvent, most preferably in a solvent selected from the group consisting of dimethylformamide, acetonitrile, dimethylacetamide and N-methylpyrrolidinone, most preferably dimethylformamide. For example 0.001 to 10 L, preferably 0.01 to 5 L, most preferably 0.05 to 1 L of solvent may be used per mol of the compound of formula (II) used in order to prepare this solution.

Preferably at this point about 0.07 to 0.5 L of solvent are used per mol of the compound of formula (II) originally put in.

The solution thus obtained is then added, over a period of for example 10 minutes to 3 hours, preferably 20 minutes to 2 hours, to stirred acetic anhydride heated to a temperature of more than 70° C., preferably more than 80° C., preferably more than 90° C., but not more than 139° C. Most preferably, the acetic anhydride used is heated to a temperature of about 120–135° C. According to the invention, for example, 1 to 10 mol, preferably 2 to 8 mol, most preferably about 3 to 6 mol of acetic anhydride are used per mol of the compound of formula (II) originally put in. Preferably, according to the invention, about 4 to 5 mol of acetic anhydride are used per mol of the compound of formula (II) put in. During this reaction $CO_2$ is given off. After the addition has ended for example a further 0.0005 to 5 L, preferably 0.005 to 2,5 L, most preferably 0.025 to 0.5 L of the abovementioned solvent are added to the solution containing the compound of formula (IV) and the resulting mixture is stirred at constant temperature for a further 10 minutes to 6 hours, for example, preferably a further 30 minutes to 3 hours, most preferably a further 1 to 2 hours. Then all the liquid ingredients of the reaction mixture are eliminated by distillation at least 40° C., preferably at least 50° C., most preferably at about 55–70° C. under reduced pressure, preferably at about 20 mbar or less, preferably at about 10 mbar or less.

The residue remaining is then taken up in a suitable solvent, preferably in water and/or a lower alcohol, selected from the group consisting of methanol, ethanol and isopropanol, most preferably water, ethanol or a mixture thereof. At this point preferably 0.1 to 3 L, most preferably about 0.5 to 2 L of one of the abovementioned alcohols mixed with for example 0.01 to 1 L, preferably 0.05 to 0.5 L of water are used as solvent, per mol of the compound of formula (II) originally put in.

To saponify the ester function of the compound of formula (V) now present in dissolved form this is combined with a suitable base. Suitable bases are preferably inorganic bases, selected from among the alkali or alkaline earth metal carbonates, alkali or alkaline earth metal alkoxides and alkali or alkaline earth metal hydroxides. Particularly preferred are the hydroxides of lithium, sodium, potassium and calcium, most preferably sodium or calcium. According to the invention sodium hydroxide is most preferably used as the base. The abovementioned bases may be used in pure form or, more preferably, in the form of aqueous concentrated solutions. If, for example, sodium hydroxide is used, which is the particularly preferred base, it is preferably added in the form of aqueous solutions with a concentration of at least 40 wt. %. It is essential to use at least stoichiometric amounts of base per mol of the compound of formula (II) originally put in. However, it is also possible to use the base in excess. Preferably, about 1.1 to 4 mol, preferably 1.5 to 3 mol, most preferably about 1.7 to 2.5 mol of the abovementioned base are used per mol of the compound of formula (II) originally used. The base may be added to the solution of the ester of formula (V) for example at a temperature in the range from 0 to 50° C. However, after the base has been added it is preferable to heat the resulting reaction mixture to a temperature above 50° C., most preferably above 60° C. In a particularly preferred embodiment of the present invention, after all the base has been added, the reaction mixture obtained is refluxed with stirring for a period of about 15 minutes to 4 hours, preferably 30 minutes to 3 hours, most preferably 1 to 2 hours. Then the solvent is eliminated by distillation at least 40° C., preferably at least 50° C., most preferably at about 50–60° C. under reduced pressure, preferably at about 80 mbar or less, preferably at about 60 mbar or less, most preferably at about 50 mbar or less.

The residue obtained is taken up in water. About 0.01 to 1, preferably about 0.1 to 1 L of water are used per mol of the compound of formula (II) originally put in. The tropenol is extracted from this mixture by means of a suitable, water-immiscible organic solvent, preferably using a solvent selected from the group consisting of toluene, methyl-tert-butylether, dichloromethane, chloroform, preferably dichloromethane. According to the invention, a total of between 0.5 and 5, preferably between 0.75 and 4 litres of organic solvent are used for the extraction per mol of the compound of formula (II) used. The extraction is carried out according to the invention between 3 and 8, preferably 4 to 6 times. After the extraction has ended the organic phases are combined and the organic solvent is distilled off in vacuo.

The crude product remaining is taken up in an organic solvent selected from among methanol, ethanol and isopropanol, preferably isopropanol. According to the invention between 0.1 and 4.0 litres, preferably between about 1 and 2 litres of this abovementioned solvent are used per mol of the compound of formula (II) originally used. The solution obtained is optionally filtered. The filtrate contains tropenol of formula (I) in the form of its free base. If the free base is to be used in the next reaction, the solvent is distilled off in vacuo at this point. The remaining free base can then be used in the next steps of the synthesis, without further purification. According to the invention, however, the free base of tropenol is preferably converted into one of the acid addition salts. By the acid addition salts of tropenol are meant, for the purposes of the present invention, the salts selected from among the hydrochloride, hydrobromide, hydrogen phosphate, hydrogen sulphate, tetrafluoroborate or hexafluorophosphate. The hydrobromide and hydrochloride salts are particularly preferred, while tropenol hydrochloride is of particular importance according to the invention. To prepare the acid addition salts the filtrate is cooled to a temperature in the range from −20° C. to 20° C., preferably in the range from −10° C. to 15° C. The suspension thus obtained is then combined with the corresponding acid needed to form the acid addition salts, namely the hydrochloride, hydrobromide, hydrogen phosphate, hydrogen sulphate, tetrafluoroborate or hexafluorophosphate. At least 1 mol of the acid in question should be used per mol of the compound of formula (II) originally used. It may be possible, within the scope of the processes according to the invention, to use the acid in excess (i.e. 1.1 to about 2–3 mol per mol of the base (II) originally used). According to the invention the hydrochloride of tropenol is preferably prepared. The hydrochloric acid required for this may be added either in the form of a solution or in gaseous form. Preferably, hydrogen chloride in gaseous form is added. One of the abovementioned acids is added to the solution of the free base of the tropenol (I) until a pH of 1 to 5, preferably 1.5 to 4, is obtained. After all the acid has been added stirring may optionally continue at constant temperature for a further 0.5 to 2 hours. Finally, the precipitated acid addition salt of tropenol is separated off and optionally washed with a solvent selected from among acetone, methylisobutylketone and methylethylketone, preferably acetone, and dried in vacuo or under an inert gas (such as nitrogen), optionally at elevated temperature.

As mentioned in the introduction, tropenol, which may be obtained by the preparation process according to the invention, is a valuable starting compound for preparing therapeutically active compounds such as for example tiotropium bromide, ipratropium bromide or BEA2108. Because of the high purity in which tropenol can be obtained according to the present invention, it is possible to prepare the abovementioned active substances in the specifications required for pharmaceutical use.

Accordingly, the present invention further relates to the use of tropenol, optionally in the form of the acid addition salts thereof, as a starting material for preparing therapeutically active compounds such as for example tiotropium bromide, ipratropium bromide or BEA2108, preferably tiotropium bromide.

optionally in the form of the hydrates thereof, as a starting material for preparing therapeutically active compounds such as for example tiotropium bromide, ipratropium bromide or BEA2108, preferably tiotropium bromide.

Preferably, the present invention relates to the use of meteloidin, optionally in the form of the acid addition salts thereof, as well as optionally in the form of its hydrates, as a starting material for preparing therapeutically active compounds such as for example tiotropium bromide, ipratropium bromide or BEA2108, preferably tiotropium bromide.

The procedure illustrated in Diagram 1 may be used to prepare tiotropium bromide starting from tropenol.

Diagram 1:

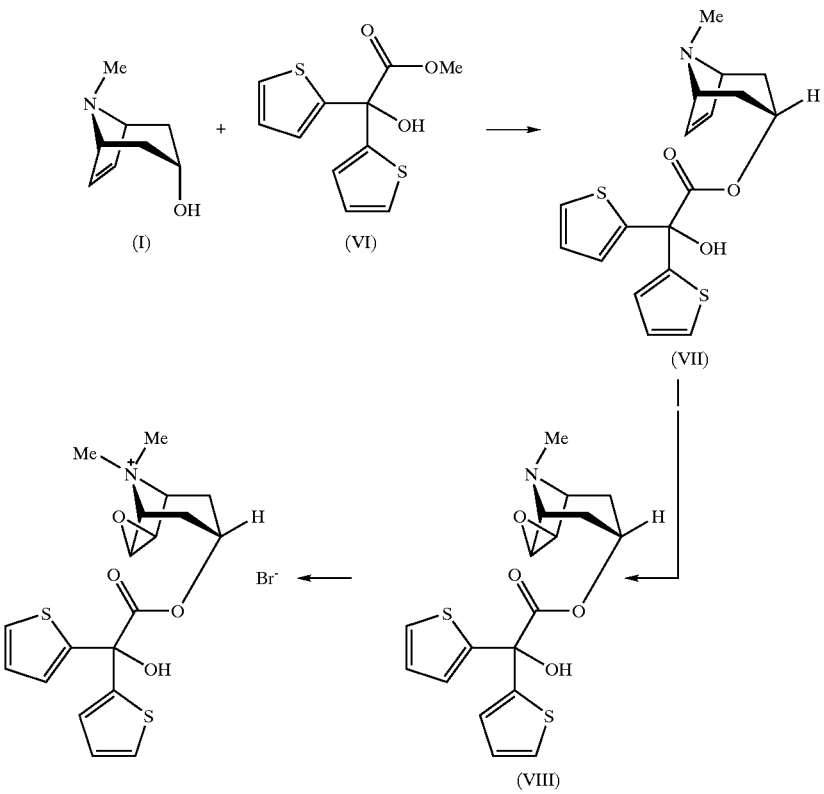

The present invention further relates to the use of compounds of formula (II)

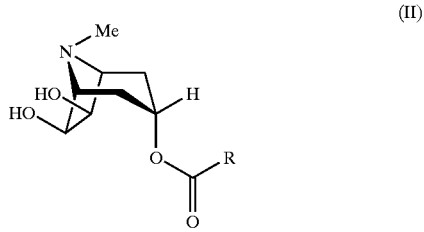

(II)

wherein R may have the meanings given above, optionally in the form of the acid addition salts thereof as well as Starting from the tropenol (I) which may be obtained according to the invention, first tropenol di-(2-thienyl)-glycolate (VII) is formed by reacting with di-(2-thienyl)-glycolic acid derivatives (VI). This ester is converted by epoxidation of the olefinic double bond into the corresponding scopine ester (VIII), from which tiotropium bromide can be obtained by reacting with methyl bromide.

Therefore, in a particularly preferred aspect, the present invention relates to a process for preparing tiotropium bromide

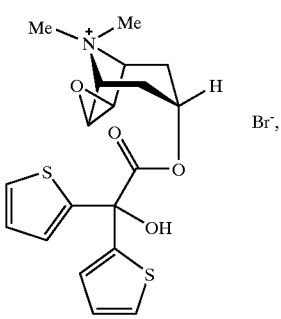

characterized in that in a first step a compound of formula (II)

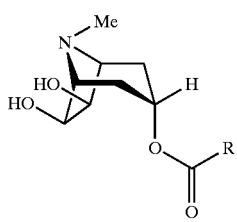

wherein R may have the meanings given above, optionally in the form of the acid addition salts thereof as well as optionally in the form of the hydrates thereof, is reacted in a suitable solvent with a formamide-acetal of formula (III)

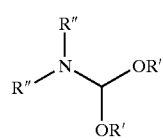

wherein

R' and R" may have the abovementioned meanings, to obtain a compound of formula IV

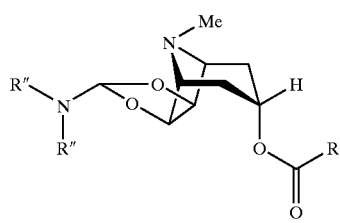

wherein the groups R, R' and R" may have the meanings given above, then this is converted by decarboxylation into an ester of formula (V)

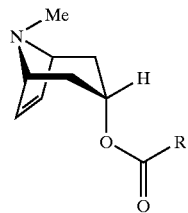

wherein R may have the meanings given above, and this ester is saponified to obtain tropenol of formula (I), which is reacted, optionally in the form of the acid addition salts thereof, in a second step with an ester of formula (VI)

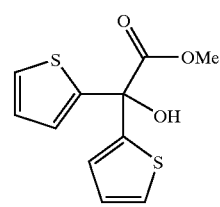

to obtain the tropenol ester of formula (VII)

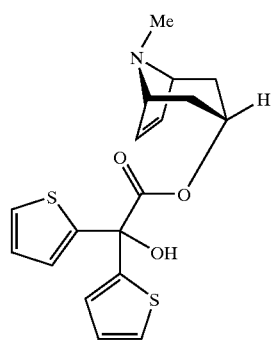

which is epoxidised in a third step to obtain the scopine ester of formula (VIII)

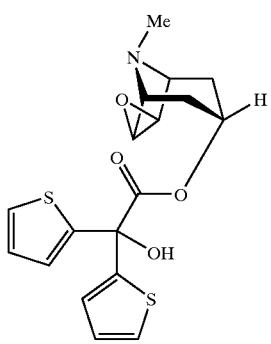

and this is then quaternised in a fourth step using methyl-bromide to obtain tiotropium bromide.

The Examples that follow serve to illustrate some methods of synthesis carried out by way of example in order to prepare tropenol and the tiotropium bromide which may be obtained therefrom. They are intended solely as possible procedures, provided as an illustration, without restricting the invention to their content.

EXAMPLE 1

Preparation of Tropenol (I) in the Form of its Hydrochloride 19.5 kg of dimethylformamide dimethylacetal are placed in a suitably sized stirred apparatus and 20.9 kg of meteloidin are added batchwise. After the addition has ended the resulting mixture is slowly heated to a temperature of about 80° C. with stirring. The methanol liberated in the course of the reaction is distilled off. After the reaction has ended the excess dimethylformamide dimethylacetal is distilled off at about 50–60° C. under reduced pressure (30 mbar or less). Then 8 L dimethylformamide are added to the residue remaining and the solution obtained is cooled to about 45–50° C. with stirring. This solution is then added, over a period of about 30–70 minutes at about 125–135° C., to 37.7 kg of stirred acetic anhydride heated to 125° C. Gaseous $CO_2$ is given off. After the addition has ended a further 4 L dimethylformamide are added and the whole reaction mixture is stirred for a further 1.5 hours at about 125–135° C. Once the reaction has ended all the liquid constituents are distilled off by heating to about 60° C. under reduced pressure (about 5 mbar or less). The residue remaining is taken up in 71 L ethanol and cooled to about 25° C. with stirring. After the addition of 8 L water and another 10 L ethanol, 45% sodium hydroxide solution (18.3 kg) is added to the resulting mixture. The mixture obtained is refluxed for about 1.5 hours with stirring. The solvent is then distilled off at about 50–60° C. under reduced pressure (about 40 mbar) and the residue remaining is taken up in 31 L water. In order to extract the product 62 L methylene chloride are added. After separation of the organic phase the aqueous phase remaining is extracted twice more with 30 L methylene chloride and 3 times with 21 L methylene chloride. The organic phases obtained are combined and the solvent is removed by distillation. The residue remaining is then taken up in about 35 kg of isopropanol, combined with 1.6 kg of Clarcel and the resulting mixture is stirred and filtered. Then at an internal temperature of about −10° C. to +10° C. gaseous hydrogen chloride is piped into the resulting solution until a pH of about 2–3 is obtained (approx. 3.0 kg of HCl gas). Once all the gas has been added the mixture is stirred for another hour or so at constant temperature. The solid formed, tropenol hydrochloride, is separated off and dried at about 40–45° C. under nitrogen.

Yield: 11.5 kg of tropenol-hydrochloride (80% based on the meteloidin used)

EXAMPLE 2

Preparation of Tiotropium Bromide a) Preparation of the Tropenol Ester (VII)

Ammonia (1.8 kg) is piped into 10.9 kg of tropenol hydrochloride (obtainable according to Example 1) in toluene (95 L) at 25° C. The resulting suspension is stirred for about 1 h at constant temperature. Then the ammonium hydrochloride formed is filtered off and rinsed with toluene (26 L). At a jacket temperature of about 50° C. some of the toluene (about 60 L) is distilled off in vacuo. After cooling to about 25° C. 15.8 kg of methyl di-(2-thienyl)glycolate are added and the resulting mixture is heated to 50° C. to dissolve it. Toluene (40 L) is placed in another apparatus and sodium hydride (2.7 kg) is added thereto at about 25° C. The previously formed solution of tropenol and methyl di-(2-thienyl)-glycolate is added to this solution at 30° C. within 1 h. After the addition has ended, the mixture is heated to 75° C. under reduced pressure for about 7 hours with stirring. The methanol formed is distilled off. The mixture remaining is cooled and added to a mixture of water (958 L) and 36% hydrochloric acid (13.2 kg). The aqueous phase is then separated off and washed with methylene chloride (56 L). After more methylene chloride has been added (198 L) the mixture thus obtained is adjusted to pH 9 with prepared soda solution (9.6 kg of soda in 45 L of water). The methylene chloride phase is separated off and the aqueous phase is stirred with methylene chloride (262 L). The methylene chloride phase is evaporated down to the residue at 65° C. The residue is taken up in toluene (166 L) and heated to 95° C. The toluene solution is cooled to 0° C. The crystals obtained are separated off, washed with toluene (33 L) and dried at about 50° C. for max. 24 hours in a nitrogen current.

Yield: 18.6 kg (83%); melting point: about 160° C. (determined by TLC at a heating rate of 10 K/min);

b) Preparation of the Scopine Ester (VIII)

260 L of DMF are placed in a suitable reaction apparatus and heated to 50° C. Then 16.2 kg of tropenol ester (IV) are added and the mixture is stirred until a clear solution is obtained. After cooling to 40° C., hydrogen peroxide-urea complex (10.2 kg), water (13 L) and vanadium-(V)-oxide (0.7 kg) are added successively batchwise and the contents of the apparatus are heated to about 50° C. After 2–3 h stirring at constant temperature the mixture is cooled to about 20° C. The reaction mixture obtained is adjusted to about pH 4.0 with hydrochloric acid (36%). Prepared sodium bisulphite solution (2.4 kg in 24 L of water) is added. At an internal temperature of 35° C. the solvent is partially distilled off in vacuo (about 210 L). It is cooled to about 20° C. again and combined with Clarcel (3.2 kg). The pH is adjusted to about 2.0 with dilute hydrochloric acid (36%, 0.8 kg in about 440 L of water). The resulting solution is filtered and extracted with methylene chloride (58 L). The methylene chloride phase is discarded. Methylene chloride (130 L) is again added to the aqueous phase and the pH is adjusted to about 10.0 with a prepared soda solution (11.0 kg in 51 L of water). The methylene chloride phase is separated off and the aqueous phase is extracted with methylene chloride (136 L). Methylene chloride (about 175 L) is distilled off from the combined methylene chloride phases in a weak vacuum (600–700 mbar) at 40° C. The contents of the apparatus are cooled to 20° C., acetyl chloride (about 0.5 kg) is added and the mixture is stirred for about 40 minutes at 20° C. The reaction solution is transferred into a second apparatus. The pH is adjusted to 2.0 with a prepared hydrochloric acid solution (4.7 kg of 36% hydrochloric acid in 460 L of water) at 20° C. The methylene chloride phase is separated off and discarded. The aqueous phase is washed with methylene chloride (39 L). Then methylene chloride (130 L) is added and the pH is adjusted to 10.0 with a prepared soda solution (7.8 kg of soda in 38 L of water) at 20° C. After 15 min. stirring the organic phase is separated off and the aqueous phase is washed twice with methylene chloride (97 L and 65 L). The methylene chloride phases are combined and some of the methylene chloride (90 L) is distilled off in a weak vacuum at a temperature of 30–40° C. Then dimethylformamide (114 kg) is added and the remainder of the methylene chloride is distilled off in vacuo at 40° C. The contents of the apparatus are cooled to 20° C.

c) Preparation of the Tiotropium Bromide

Methyl bromide (5.1 kg) is piped into the scopine ester solution obtained by the method described above at 20° C. The contents of the apparatus are stirred at 30° C. for about 2.5 days. 70 L of DMF are distilled off at 50° C. in vacuo. The solution is transferred into a smaller apparatus. It is rinsed with DMF (10 L). Additional DMF is distilled off at 50° C. in vacuo until a total amount of distillate of about 100 L is obtained. This is cooled to 15° C. and stirred for 2 hours at this temperature. The product is isolated using a suction filter drier, washed with 15° C. cold DMF (10 L) and 15° C. cold acetone (25 L). It is dried at max. 50° C. for max. 36 hours in a nitrogen current. Yield: 13.2 kg (88%);

Melting point: 200–230° C. (depending on the purity of the starting product);

The crude product thus obtained (10.3 kg) is added to methanol (66 L). The mixture is refluxed to dissolve it. The solution is cooled to 7° C. and stirred for 1.5 h at this temperature. The product is isolated using a suction filter drier, washed with 7° C. cold methanol (11 L) and dried for max. 36 h at about 50° C. in a nitrogen current.

Yield: 9.9 kg (96%); Melting point: 228° C. (determined by TLC at a heating rate of 10 K/min).

If desired, the product thus obtained may be converted in the crystalline monohydrate of tiotropium bromide. The following method may be used.

15.0 kg of tiotropium bromide are added to 25.7 kg of water in a suitable reaction vessel. The mixture is heated to 80–90° C. and stirred at constant temperature until a clear solution is formed. Activated charcoal (0.8 kg), moistened with water, is suspended in 4.4 kg of water, this mixture is added to the solution containing tiotropium bromide and rinsed with 4.3 kg of water. The mixture thus obtained is stirred for at least 15 min. at 80–90° C. and then filtered through a heated filter into an apparatus which has been preheated to an outer temperature of 70° C. The filter is rinsed with 8.6 kg of water. The contents of the apparatus are cooled to a temperature of 20–25° C. at a rate of 3–5° C. every 20 minutes. Using cold water the apparatus is cooled further to 10–15° C. and crystallisation is completed by stirring for at least another hour. The crystals are isolated using a suction filter drier, the crystal slurry isolated is washed with 9 L of cold water (10–15° C.) and cold acetone (10–15° C.). The crystals obtained are dried at 25° C. for 2 hours in a nitrogen current.

Yield: 13.4 kg of tiotropium bromide monohydrate (86% of theory). Melting point: 230° C. (determined by TLC at a heating rate of 10 K/min).

We claim:

1. A compound of formula IV

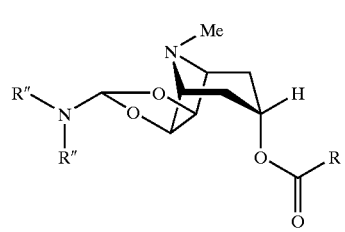

wherein R denotes a group selected from $C_1$–$C_4$-alkyl, $C_2$–$C_6$-alkenyl and $C_1$–$C_4$-alkylene-phenyl, each of which is optionally substituted by hydroxy or $C_1$–$C_4$-alkoxy, optionally in the form of the acid addition salts thereof or the hydrates thereof.

2. The compound according to claim 1 wherein R is selected from the group consisting of 1-propenyl, 2-propenyl, 1-buten-1-yl, 1-buten-2-yl, 1-buten-3-yl, 1-buten-4-yl, 2-buten-1-yl and 2-buten-2-yl.

3. The compound according to claim 2 wherein R is 2-buten-2-yl.

4. The compound according to claim 1 wherein R is 2-buten-2-yl and $R_2$ is methyl.

* * * * *